(12) United States Patent
Fullam et al.

(10) Patent No.: US 7,757,635 B2
(45) Date of Patent: Jul. 20, 2010

(54) METHOD AND APPARATUS FOR DETECTING MASTITIS

(75) Inventors: Philip Stephen Fullam, San Antonio, TX (US); David Kent Wright, Leominster (GB)

(73) Assignee: Krysium Advisors Limited, Leominster (GB)

( * ) Notice: Subject to any disclaimer, the term of this patent is extended or adjusted under 35 U.S.C. 154(b) by 477 days.

(21) Appl. No.: 10/535,713

(22) PCT Filed: Nov. 19, 2003

(86) PCT No.: PCT/GB03/05029

§ 371 (c)(1),
(2), (4) Date: Feb. 2, 2006

(87) PCT Pub. No.: WO2004/048968

PCT Pub. Date: Jun. 10, 2004

(65) Prior Publication Data

US 2006/0124064 A1    Jun. 15, 2006

(30) Foreign Application Priority Data

Nov. 22, 2002   (GB) ................................ 0227296.1

(51) Int. Cl.
*A01J 5/007* (2006.01)
*A01J 5/013* (2006.01)

(52) U.S. Cl. .................. 119/14.14; 119/14.18

(58) Field of Classification Search ............ 119/14.14, 119/14.18; A01J 05/13
See application file for complete search history.

(56) References Cited

U.S. PATENT DOCUMENTS

| 5,804,370 | A | 9/1998 | Romaschin | |
| 6,297,045 | B1 * | 10/2001 | Takahashi et al. | 435/288.7 |
| 6,814,025 | B2 * | 11/2004 | Chen et al. | 119/14.01 |
| 6,981,466 | B2 * | 1/2006 | Lindholm | 119/14.02 |
| 7,236,237 | B2 * | 6/2007 | Schmilovitch et al. | 356/73 |
| 2005/0217587 | A1 * | 10/2005 | Nelson et al. | 119/14.02 |

FOREIGN PATENT DOCUMENTS

| EP | 0 489 602 A | 6/1992 |
| GB | 1 315 467 A | 4/1971 |
| GB | 2 001 434 A | 1/1979 |
| GB | 2 350421 A | 5/1999 |
| WO | WO 88/07584 A | 10/1988 |
| WO | WO 01/35728 A | 5/2001 |
| WO | WO 2004061436 A1 * | 1/2004 |

* cited by examiner

*Primary Examiner*—Rob Swiatek
*Assistant Examiner*—Kristen C Hayes
(74) *Attorney, Agent, or Firm*—Egbert Law Offices PLLC

(57) ABSTRACT

A method of testing a biological fluid for the presence of an infection. The method includes the steps of introducing a sample of biological fluid and a reagent including light amplifying compound into a reaction chamber, the light amplifying compound reacting with a substance present only in an infected sample to emit light, and immediately measuring the intensity of any light emitted from the sample.

8 Claims, 3 Drawing Sheets

METHOD AND APPARATUS FOR DETECTING MASTITIS

DESCRIPTION OF INVENTION

The present invention relates to a method of and apparatus for testing a biological fluid.

It is known to test a biological fluid for the presence of bacteria cells or somatic cells in the fluid. Such a test may be carried on milk produced by dairy cows and other mammals to determine whether the animal is suffering from mastitis. For example, laboratory testing of milk samples taken by milk collection operatives is regularly carried out.

Known such tests may involve determining the number of bacteria cells or somatic cells in the sample for a direct indication of the presence of mastitis. The standard test method involves the use of a flow cytometer to count the bacteria in a fluid sample. As the cost of the necessary equipment and the skill level required to maintain the equipment is high, and use of the equipment requires a controlled environment, this method is generally performed in a dedicated laboratory. Alternatively, bacteria or somatic cell levels may be determined by microscopic examination of a milk sample using dyes to enhance cell visibility. Such a test is, however, very time consuming and must be carried out by a highly trained technician, and is generally suitable only for use in a laboratory environment.

Indirect test methods may also be used, for example determining the level of other biological agents such as enzymes, proteins, or other organic compounds in a sample. As these methods rely on the use of very precise amounts and concentrations of reagents, they are most suited to use in a laboratory, although carefully designed and packaged kits can be used to carry out such methods in a farm environment, as illustrated in our UK patent application GB2350421.

A problem with known laboratory based testing is that there is inevitably a delay between when the sample is taken and when the test results are available. Mastitis can progress rapidly and so the test results may not be accurately indicative of the state of the disease when for example the animal is next milked. Also a laboratory based test on a sample taken by a collection operative (tanker driver), is most likely to include milk produced by a plurality of animals. Thus such tests, whilst, being of some use in determining milk quality from a particular farm, are not useful in advising a dairyman for example, as to which of his animals is suffering from mastitis.

Thus a dairyman needs to be able to perform tests on individual animals which will give a rapid result, so that the dairyman can be alerted to an animal which is suffering from mastitis. In response, the dairyman may decide to dispose of an individual animal's milk so as not to lower the quality of milk from the herd, and may make a decision either to treat the animal e.g. with antibiotics, or to allow the animal's own immune system to combat the infection.

In each case, early diagnosis of mastitis is important to enable the dairyman proactively to maintain the quality of the herd's milk provided for production, to provide for timely, appropriate treatment of individual animals in the herd, and to maintain expected milk quality.

Milk tests are known which are intended to be performed by a dairyman, and these include the Californian Mastitis Test (CMT) or the Wisconsin Mastitis Test (WMT). However to perform such tests, the tester needs to make subjective judgements which a dairyman may not be sufficiently skilled to make. Also such tests exhibit a lack of sensitivity for detecting subclinical mastitis, and lack accuracy at somatic cell count levels required by current rules and regulations.

Another test method which may be used in the field is the conductivity test, in which a DC voltage is applied across a milk sample, and the resulting current measured. The current gives some indication of the quality of the sample, but the current is also strongly affected by other variables such as temperature and changes in diet of the cow, and therefore the results are not regarded as particularly accurate or reliable.

As mentioned above, portable, carefully designed and packaged test kits for use by a dairyman in the field, which produce accurate and reliable test results are known, but these too require the dairyman to take the time to carry out the test and to note the results.

Economic pressures on farmers are ever increasing, and, particularly on large farms, milking is becoming ever more automated and comparable to an industrial production line. There is pressure to reduce the time required to milk each cow, and to reduce the amount of human intervention required. Thus, there is a need for a fully automated milk testing method which can be incorporated into the milking "production line" and used to test the milk from each cow every day, or even every milking, without requiring a dairyman to spend time testing each animal.

The conductivity test method has been incorporated into automatic milking systems, but as discussed above, the results are inaccurate and unreliable.

U.S. Pat. No. 6,297,045 discloses an apparatus and method for testing milk samples in which mastitis is detected by measuring the level of intensity of light chemically emitted by phagocytic leukocytes when they phagocytose bacteria in the milk sample. When an infection is detected by the body, the body uses phagocytic leukocytes such as neutrophils as the first line of attack against the infection. Thus, the number of neutrophils in a sample gives an indication as to whether infection is present.

Neutrophils engulf and digest bacterial cells in a process known as phagocytosis. During this process, active oxygen, or "superoxide" intermediates are produced and play a role in killing the bacteria. The superoxides are highly reactive and will react with light amplifiers such as luminol to produce photons of light in proportion of the amount of superoxide released. In the test method of U.S. Pat. No. 6,297,045, a phagocyte stimulator zymosan is added to induce, phagocytic reaction in the neutrophils present in the sample, and the sample is incubated, typically for about 20 minutes, to allow time for the neutrophils to respond to the phagocytic stimulator before light measurements are commenced. Thus the test, which requires a stimulator such as zymosan is essentially an in vitro test.

Thus, by measuring the amount of light emitted, the number of neutrophils in a sample, and hence the degree of infection, can be determined.

Because the test requires an incubation time of at least 20 minutes, to allow the phagocyte stimulator to take effect, this test takes too long for it to be usefully incorporated in an automated milking system.

According to a first aspect of the invention we provide a method of testing a biological fluid for the presence of an infection, the method including the steps of introducing a sample of biological fluid and a reagent including light amplifying compound into a reaction chamber, the light amplifying compound reacting with a substance present only in an infected sample to emit light, and immediately measuring the intensity of any light emitted from the sample.

Thus the method of the invention provides a test which does not require the use of any stimulator. Rather, the test is essentially an in vivo test, looking at the results of the phagocytic reaction as soon as possible after mixing the samples and reagent, by measuring the superoxide concentration.

Preferably the light amplifying compound reacts with a compound produced by phagocytic leukocytes in response to infection to emit light.

Preferably the light amplifying compound reacts with a compound produced when phagocytic leukocytes phagocytose bacteria to emit light.

Further preferably, the light amplifying compound reacts with reactive oxygen to emit light.

It has been found that neutrophils in a biological fluid sample from an infected animal are phagocytically active when the sample is collected, and the superoxide produced by such neutrophils reacts with the light amplifier to produce an initial light burst. No such light burst is produced from a biological fluid sample from a healthy animal.

The burst of light is of relatively short duration, and therefore light measurements must be commenced immediately. Consequently, testing may be completed within around 1 minute, and therefore the invention provides a rapid method of testing for the presence of diseases in animals, such as mastitis, which is suitable for incorporation into an automated milking system.

Preferably the intensity of light emitted from the sample is measured up to a maximum of five or preferably three minutes after the adding of the reagent to the sample.

Preferably, the method further includes the step of recording the intensity of light emitted by the sample using a data recording and processing device such as a PC.

Preferably the intensity of light emitted from the sample is measured using a photodiode.

Preferably the light amplifier is luminol.

The reagent preferably further includes a pH buffered iron solution, e.g. to increase the light output of the light amplifier which typically is luminol.

The method may further include the steps of connecting a first inlet port of generally a fluid and light tight reaction chamber of variable capacity to a milk line in an automated milking system, connecting a second inlet port of the reaction chamber to a supply of reagent, increasing the capacity of the chamber in order to draw milk and reagent into the chamber.

Thus, the method allows testing of milk within an automated system to be carried without human intervention.

The method may further include the step of controlling electrically operating valves provided in the inlet ports to regulate the proportion of reagent and sample drawn into the reaction chamber.

The capacity of the reaction chamber may be increased by movement of a piston, in which case, the piston may be actuated by means of an electrical solenoid.

According to a second aspect of the invention we provide a method of testing for mastitis in an animal, the method including the steps of collecting a sample of milk from the animal, introducing the milk sample and a reagent including a light amplifying compound into a reaction chamber, the light amplifying compound reacting with a substance present only in an infected sample to emit light, and immediately measuring the intensity of light emitted by the sample.

Preferably the light amplifying compound reacts with reactive oxygen produced when phagocytic leukocytes phagocytose bacteria.

According to a third aspect of the invention we provide an apparatus for testing milk in an automated milking system, the apparatus including a generally fluid and light tight chamber of variable capacity including an inlet port and an outlet port, means to increase the capacity of the chamber in order to draw fluid into the chamber from the inlet port or to decrease the capacity of the chamber to expel fluid in the chamber through the outlet port and a light detector to detect any light emitted from the fluid in the chamber.

Preferably the chamber is provided with two inlet ports, one of which is connected to the milk line, and the other of which is connected to a source of reagent including a light amplifying compound, the light amplifying compound reacting with a substance present only in an infected sample to emit light.

By virtue of this aspect of the invention, testing of milk within an automated system may easily be carried without human intervention. The combination of means for drawing fluid into the chamber and expelling fluid from the chamber, and light detector into a single unit simplifies construction and hence reduces the cost of such a testing system.

Preferably the inlet ports include electrically operated valves which may be operated by a controller automatically to regulate the proportion of reagent and sample drawn into the chamber.

Alternatively, the inlet ports may include valves which are metered to ensure that the required proportion of sample and reagent are drawn into the chamber.

The means to increase or decrease the capacity of the chamber may be a piston, in which case, the piston may be actuated by means of an electrical solenoid.

The light detector may be a photodiode, or another solid state light detection device, or a photomultiplier.

The light detector is preferably connected to a data recording a processing device such as a PC.

According to a fourth aspect of the invention, a milk line is provided for an automatic milking system, the milk line including a conduit for milk, a generally fluid and light tight chamber of variable capacity including an inlet port and an outlet port, the inlet port being connected to the milk conduit by means of an auxiliary milk conduit, means to increase the capacity of the chamber in order to draw milk into the chamber from the milk conduit via the inlet port or to decrease the capacity of the. chamber to expel fluid in the chamber through the outlet port, and a light detector to detect any light emitted from the fluid in the chamber.

According to a fifth aspect of the invention, an automatic milking system is provided, including a generally fluid and light tight chamber of variable capacity including an inlet port and an outlet port, means to increase the capacity of the chamber in order to draw milk into the chamber from a conduit for milk via the inlet port or to decrease the capacity of the chamber to expel fluid in the chamber through the outlet port, and a light detector to detect any light emitted from the fluid in the chamber.

Preferably the inlet port is connected to the main milk conduit by means of an auxiliary milk conduit.

Preferably the miffing system further includes a data processing apparatus, such as a PC, which is connected to the light detector and which is programmed to record the amount of light detected by the light detector, to compare the results with standard data and to provide an indication as to whether the milk has been taken from an animal with mastitis.

The data processing apparatus may be connected to a visual display apparatus adapted to provide a visual warning that mastitis has been detected. Alternatively, or additionally, the data processing apparatus may be connected to an audible warning device adapted to provide an audible warning that mastitis has been detected.

Preferably the chamber is provided with two inlet ports, one of which is connected to the milk conduit, and the other of which is connected to a source of reagent including a light amplifying compound, the light amplifying compound reacting with a substance present only in an infected sample to emit light.

Preferably the inlet ports include electrically operated valves and the milking system further includes a controller adapted to control the valves automatically to regulate the proportion of reagent and sample drawn into the chamber.

Alternatively, the inlet ports may include valves which are metered to ensure that the required proportion of sample and reagent are drawn into the chamber.

The invention will now be described with reference to and/or as shown in the accompanying drawings.

A sample of biological fluid is collected. In this case, the biological fluid is milk, and a 0.1 mL sample is preferably taken directly from the milk line and automatically introduced into the reaction chamber.

A liquid reagent including a light amplifier, in this case 5 mM/L luminol, an iron rich pH buffer, solution (1 mM/L Fe and 25 mM/L Tris Buffer), and reagent grade water, is added to the sample. This is done in a temperature controlled chamber whose temperature is held above 35° C. and preferably below 45° C.

Figure 1:
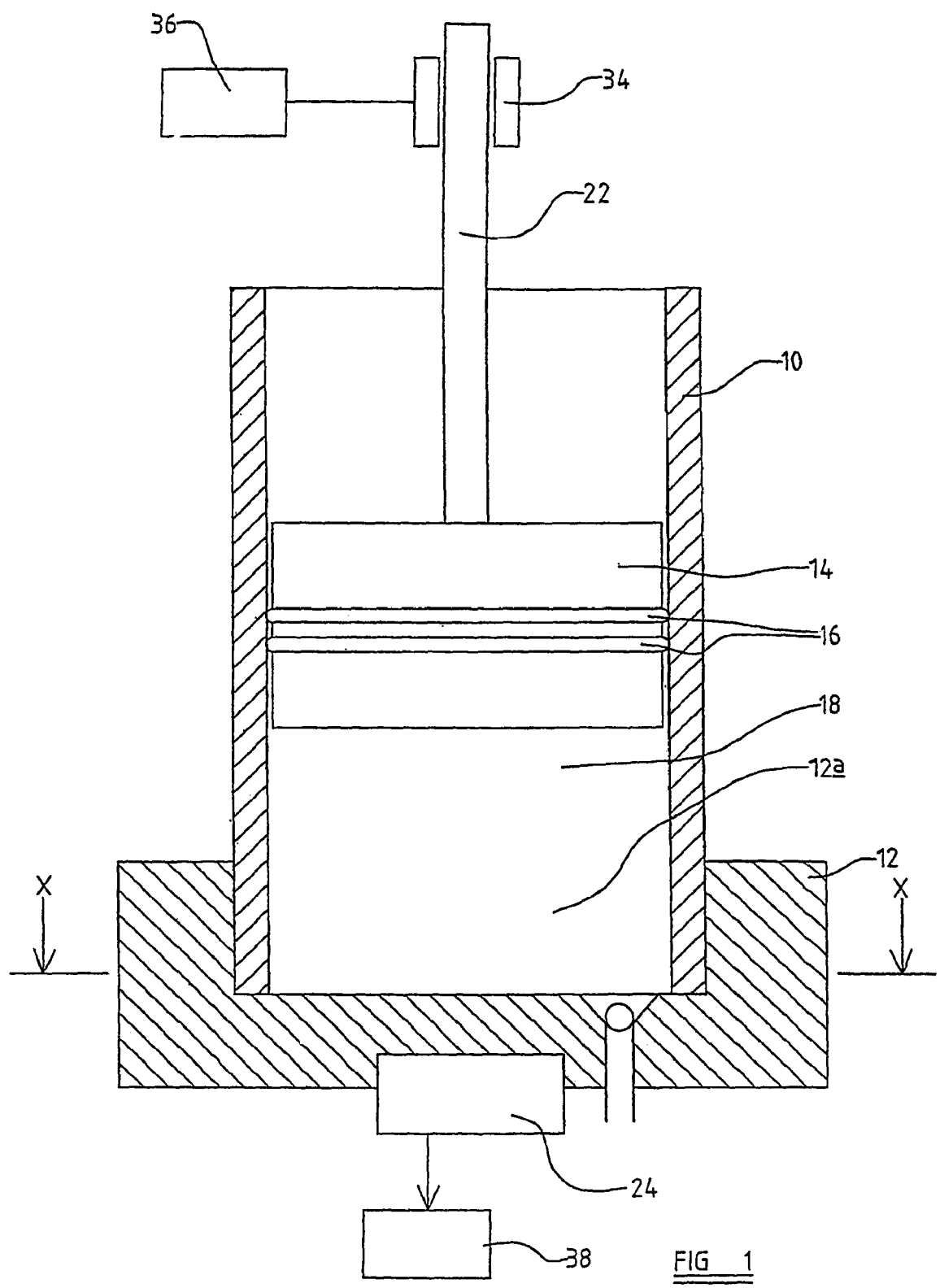
FIG. 1 is a schematic view of an illustration of an apparatus for testing a biological fluid according to the third aspect of the invention.
Figure 2:
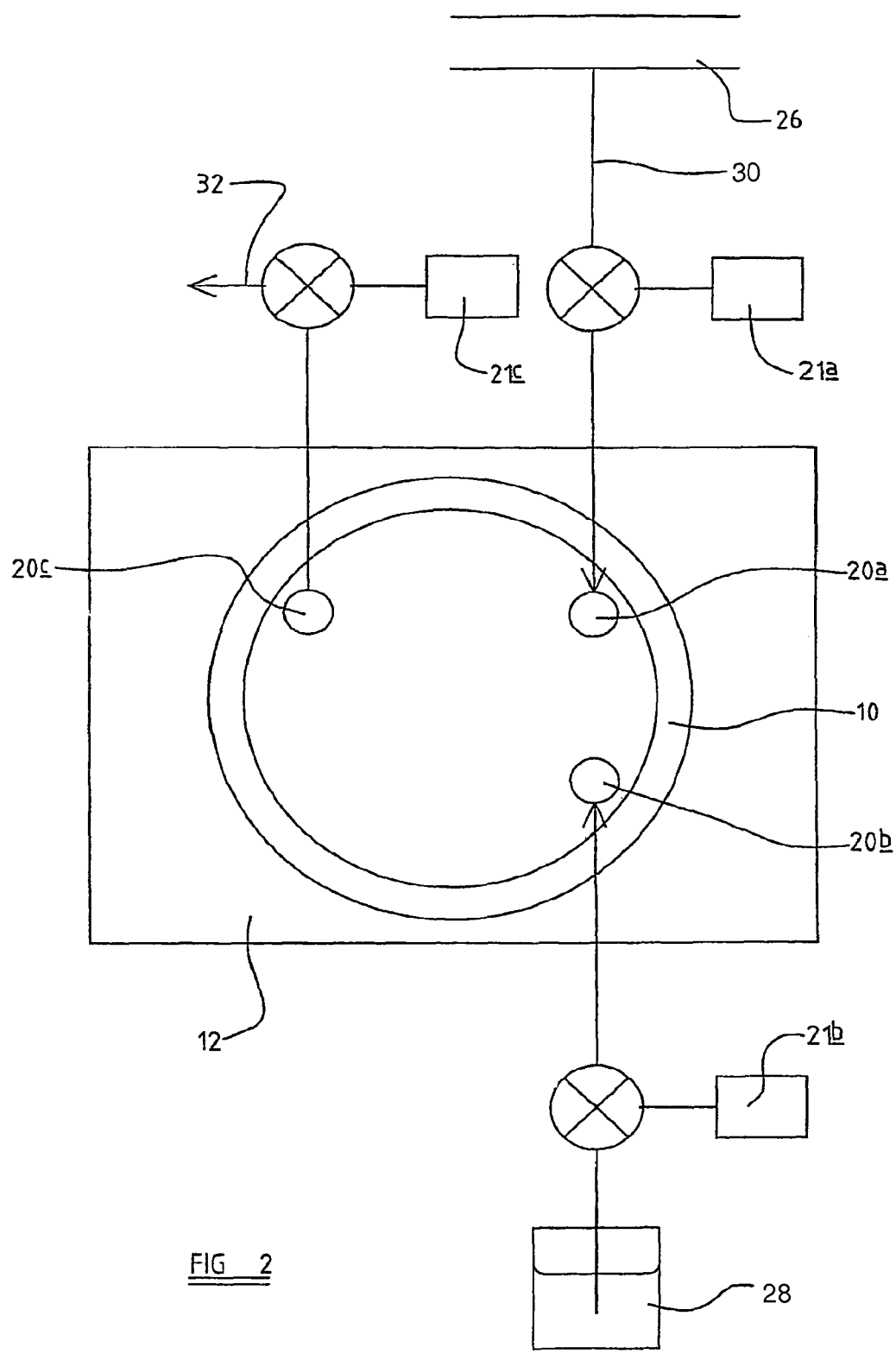
FIG. 2 is another schematic view of an illustration of a section of the apparatus of FIG. 1 along line X in FIG. 1.

An example of an apparatus used to collect the milk sample and introduce the reagent into the sample is illustrated in FIGS. 1 and 2.

Referring to the figures there is shown a cylindrical tube 10 made from an opaque and biologically inert material such as stainless steel, a lower end of which is located in a correspondingly dimensioned cylindrical recess 12a in a base 12 made from a transparent polymeric material, the base 12 substantially sealing the lower end of the tube 10.

A piston 14 is located within the tube 10, and two O-rings 16 are mounted in grooves around the circumference of the piston 14 and provide a substantially fluid tight seal between the piston 14 and the tube 10 whilst still permitting movement of the piston 14 relative to the tube 10. A reaction chamber 18 is thus formed in the tube 10 between the piston 14 and the base 12.

A light detector 24 is mounted in the base 12. In this example, the light detector is a photo diode, as this is a low cost component which has been found to be capable of detecting the light intensities typically emitted by the sample. The surface of the recess 12a in the base 12 is coated with an opaque material, other than a window portion adjacent to the light detector 24. Thus the reaction chamber 18 is generally light tight, other than a window allowing light to fall on the light detector 24.

The base 12 is provided with three ports 20a, 20b, 20c, each of which is provided with an electrical valve operable by means of a controller 21a, 21b, 21c to open or close the port 20a, 20b, 20c.

The first port 20a is connected to a supply of biological fluid, in this case, to a milk conduit 26 in an automatic milking system via an auxiliary milk conduit 30, the auxiliary milk conduit 30 being typically connected to the main milk conduit 26 between a vacuum source used to draw milk from the cow and a milking cluster on the cow's udder, the second port 20b is connected to a supply of reagent 28, and the third port 20c is connected-to a waste outlet 32.

Preferably the reaction chamber 18 is connected to a source of milk from a single cow only, so that the milk from each individual cow is tested. It would be possible, however, to connect the reaction chamber 18 to be connected to a source of milk from a plurality of cows mixed together, for example by drawing the milk sample from the central milk collection tank, but in this case, the test would merely identify that one or more cows in the herd is/are infected, and would not indicate which cow or cows were infected.

The piston 14 is connected to an actuator 34 such as a solenoid by means of a shaft 22, and the activation of the actuator 34 is controlled by a further controller 36.

A milk sample and reagent are drawn into the reaction chamber 18 by opening the valves in the first 20a and second 20b ports, and activating the actuator 34 to move the piston 14 upwards in the tube 10.

In order to prevent the milk sample itself from preventing light from reaching the light detector, the concentration of the reagent is selected such that the volume of the reagent used is approximately three times the volume of the milk sample. Thus, for a 0.1 mL milk sample, 0.3 mL of reagent is used. This has been found to reduce the opacity of the milk sample to a sufficient degree to allow as much light emitted by the sample as possible to reach the light detector.

In order to ensure that the correct proportion of sample and reagent are introduced into the reaction chamber 18, the valve on the first port 20a may be controlled to remain open for longer than the valve on the second port 20b. Alternatively, the valves may have metering orifices such that the required proportions of fluid is delivered whilst both are open for the same length of time.

Once the required amount of sample and reagent have been introduced into the reaction chamber 18, the valves are activated to close the inlet ports 20a, 20b. The light detector is immediately activated and light measurement is continued typically for up to 3 minutes although for reasons explained below, results can be obtained within the first 10 seconds although if monitoring is maintained for an additional 60-180 seconds, the method may detect very low levels of infection. The light intensity over this time period is recorded and processed to produce a graph of light output against time using a data recording and processing device 38 such as a PC. The resulting graph is then compared with a comparable plot obtained using milk from a healthy animal to determine whether the animal has mastitis.

Information regarding the expected output for a sample from a healthy animal is preferably stored in the memory of the PC 38, and the PC 38 is preferably programmed to make the necessary comparison and to provide an output signal indicating whether the animal is healthy or infected. The output signal may be displayed on a visual display device such as a PC monitor, or in a more simple system, the presence of an infected animal may be indicated using a warning light, or by means of an audible indicator device such as a buzzer or alarm bell.

The PC 38 be connected to a plurality of testing apparatus, and may therefore collect and process data from the milk samples of a plurality of cows, in which case it would be necessary for a visual display device to provide means of identifying which cow is infected.

When the test is complete, the valve in the third port 20c is opened and the actuator 34 activated to move the piston 14 downwards in the tube 10 to expel the sample and reagent mixture into the waste outlet 32. The reaction chamber 18 may be cleaned once milking is completed by drawing cleaning fluid in from the main milk line 26 during cleaning of the entire milking system, and expelling the cleaning fluid through the outlet port 20c.

When an animal has clinical mastitis, and is therefore producing increased numbers of neutrophils in response to the infectious agent, then phagocytosis was already taking place before the sample is mixed with the reagent. When the reagent is mixed with the sample, the light amplifier reacts with the superoxides already produced during phagocytosis and produces light. Thus, light is detected as soon as the light measurements are started, and the light output therefore is at a peak immediately the milk sample and reagent containing light amplifying compound are mixed, when light measurements are started, and light output decreases rapidly to reach a background level after several minutes of testing.

Figure 3A:
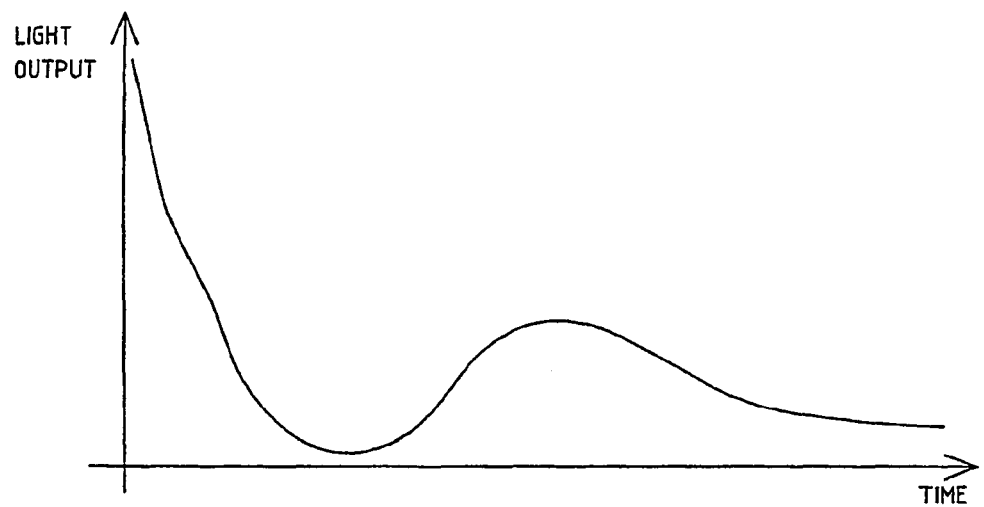
FIGS. 3a-3b are graphic illustrations of typical graphs of light output versus time produced using the method of the first and second aspects of the invention.
Figure 3B:
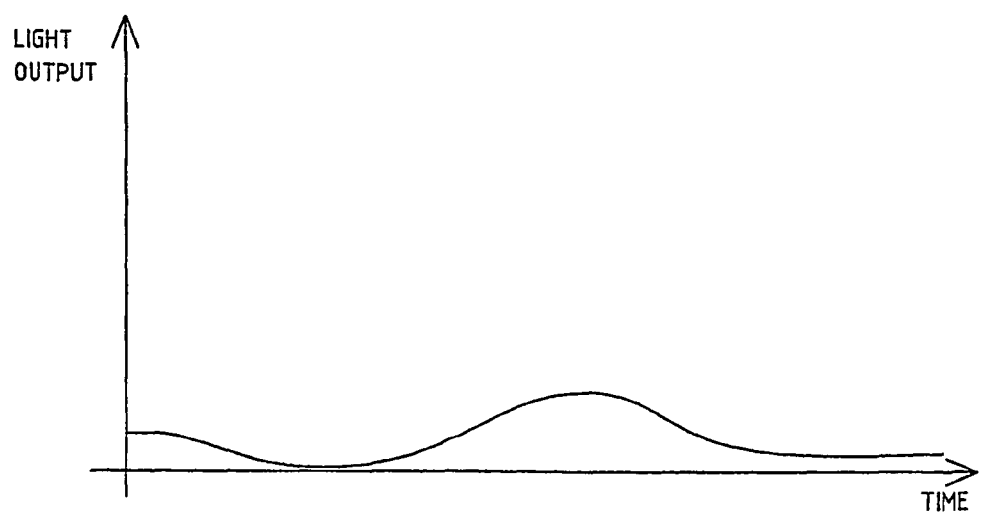

A typical plot of light output versus time for an animal with mastitis is shown in FIG. 3a.

Thus, the presence of the initial peak in light output provides an indication that an animal has an infection such as mastitis.

Moreover, the area under the light output peak provides an indication of the number of neutrophils in the sample. Thus, where the light output is recorded using a PC, the PC is preferably programmed to integrate the light output versus time curve, compare the results with standard data, and calculate and display the number of neutrophils in the sample.

The apparatus used to carry out the test is preferably calibrated and verified using positive controls such as luminol diluted in hydrogen peroxide, as this produces a light output similar to milk.

Experiments have shown that it is possible to detect neutrophil concentrations as low as 100,000 cells per mL using the method of the invention, and above the level of 300,000 cells per mL, the accuracy of the test is high and matches the accuracy of current best laboratory based tests.

Preferably the test should be carried out as soon as possible after collection of the sample, as it has been found that the accuracy and reliability of the results decreases as the length of time between collecting the sample and carrying out the test increases. It is believed that this is as a result of superoxide concentrations decreasing with time.

Preferably the data processing apparatus 38, and the controllers 36, 21a, 21b, 21c for the actuator 34 and valves are combined in a single integrated control unit, which may be separate from or integrated with a control unit for controlling the vacuum source and the other apparatus used in the milking process.

It is not necessary to use luminol as the light amplifier. Other suitable substances such as lucigenin, Vargula hilgendorfi luciferin derivatives, or a photoprotein may alternatively be used.

In the method of the invention, it is not necessary to include a phagocyte stimulator in the reagent. In order to reduce the time taken to complete a test, it is possible to base a diagnosis solely on the presence or absence of the initial light burst.

Various other modifications may be made without departing from the scope of the invention. For example, although the method of the invention has been described with particular reference to an in-line milk testing method, the method of the invention may be utilised in a non-in-line situation such as in a laboratory.

With suitable apparatus the invention may be utilised to provide quantitative test results rather than merely qualitative ranges of results.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A method of testing milk from a mammal for a presence of an infection in the mammal, the method comprising:
   forming a reaction chamber having an interior volume;
   increasing said interior volume of said reaction chamber so as to draw a liquid sample of the milk directly from a milk line of an automated milking system into said interior volume of said reaction chamber;
   drawing a reagent into said interior volume of said reaction chamber, said reagent having a light-amplifying compound therein;
   reacting said light-amplified compound with a substance produced by cells of the mammal in response to the infection prior to the liquid sample being introduced into said reaction chamber;
   activating a light detector to a measure a peak of emitted light from a reaction between the light-amplifying compound and the substance produced by the cells, the step of activating the light detector being immediately after the steps of drawing the liquid sample of the milk and drawing the reagent.

2. The method of claim 1, the substance produced by the cells of the mammal in response to the infection being produced by phagocytic leukocytes.

3. The method of claim 2, the substance produced by the cells of the mammal in response to the infection being produced when phagocytic leukocytes phagocytose bacteria.

4. The method of claim 3, said tubular member having a first inlet port and a second inlet port, the method further comprising:
   connecting the first inlet port to the milk line of the automated milking system; and
   connecting the second inlet port to a supply of said reagent.

5. The method of claim 4, further comprising:
   connecting electrically-actuated operating valves respectively to said first and second inlet ports; and
   controlling said operating valves to regulate a proportion of said reagent and the milk drawn into said reaction chamber.

6. The method of claim 1, said light-amplifying compound reacting with reactive oxygen so as to emit light.

7. The method of claim 1, the step of activating comprising:
   measuring an intensity of emitted light for a maximum of five minutes.

8. The method of claim 1, said reaction chamber being a tubular member having a piston positioned in sealed relation with an inner wall of said tubular member, said tubular member being fluid-tight and light-tight, the step of increasing said interior volume comprising:
   moving said piston upwardly in said tubular member.

* * * * *